United States Patent [19]

Morency

[11] Patent Number: 6,119,030
[45] Date of Patent: Sep. 12, 2000

[54] SILICONE TIP FOR MULTIPLE ELECTRODE BASKET ASSEMBLIES

[75] Inventor: Steven Morency, Sunnyvale, Calif.

[73] Assignee: EP Technologies, Inc., San Jose, Calif.

[21] Appl. No.: 09/102,172

[22] Filed: Jun. 22, 1998

[51] Int. Cl.[7] .................................................. A61B 5/042
[52] U.S. Cl. ........................... 600/374; 600/393; 607/122
[58] Field of Search .................................... 600/374, 393; 606/41; 607/122

[56] References Cited

U.S. PATENT DOCUMENTS 5,893,847   4/1999   Kordis ...................................... 600/374

Primary Examiner—Lee Cohen
Attorney, Agent, or Firm—Lyon & Lyon LLP

[57] ABSTRACT

A distal tip for securing a plurality of spline elements to form a catheter basket assembly is formed from a flexible, resilient material, such as silicone. The distal tip includes a plurality of passages extending radially therethrough for receiving individual spline elements, the passages intersecting an axis and spaced apart circumferentially and axially from one another with respect to the axis. The distal tip may be formed by wrapping the spline elements around a tool, such that their midpoints intersect within a cavity in the tool. An uncured material is introduced into the cavity, and then cured to form the plurality of spline passages directly around the spline elements. During use, the spline elements may be directed between contracted and expanded conditions, with the distal tip resiliently yielding and thereby minimizing stress in the spline elements.

5 Claims, 2 Drawing Sheets

SILICONE TIP FOR MULTIPLE ELECTRODE BASKET ASSEMBLIES

FIELD OF THE INVENTION

The present invention relates generally to distal assemblies for electrophysiology catheters, and more particularly to a flexible distal tip for multiple electrode basket assemblies.

BACKGROUND

Within the electrophysiology art, it is well known to provide an expandable "basket assembly" carrying multiple electrodes on the distal end of a catheter for use in a variety of diagnostic and other procedures within the heart. For example, the Constellation™ catheter manufactured by the assignee of the present application includes a distally mounted basket assembly formed by a plurality of circular spline elements attached at both ends to a catheter, i.e., such that each spline element forms a loop at the catheter end. The spline elements are generally rectangular and are made of a highly flexible metal alloy, e.g. Nitinol, which has well known shape memory properties. In particular, the spline elements are attached to the catheter end in an evenly spaced relationship, aligned like the lines of longitude on a globe.

The spline elements are joined distally, i.e., at their midpoints, by a cylindrical metal tip member. The distal tip member has a plurality of passages extending through the cylindrical body perpendicular to its longitudinal axis and spaced apart from one another. The passages intersect the longitudinal axis such that the passages are circumferentially spaced evenly about the longitudinal axis, i.e. to define evenly distributed lines of longitude on the globe.

During assembly, the spline elements are individually directed through respective passages in the tip member until their midpoints intersect the longitudinal axis, i.e., prior to being attached to the end of the catheter. Each passage includes a recess for securing a notch formed at the midpoint of the respective spline element. Thus, the cooperating notches and recesses hold the spline elements and keep them from sliding out of the passages and becoming misaligned, while still allowing for bending.

During use, the basket assembly is directed between contracted and expanded conditions. In particular, the spline elements are compressed into a contracted condition as the assembly is moved through a guide sheath for introduction into a patient's body, e.g. through the cardiovascular system. The basket assembly is deployed at a target site within the body, e.g. within a heart chamber, wherein the guide sheath is pulled back, allowing the spline elements to return to their expanded condition for use, for example, during a diagnostic procedure. During the procedure, the basket assembly may also be at least partially contracted and expanded repeatedly, for example, as a result of the beating of the heart.

To minimize the stress experienced by the spline elements during expansion and contraction, each spline element preferably defines an individual "bridge," i.e., each spline element is independently supported between the catheter body and the distal tip member, isolated from one another. For this reason, each passage through the tip member includes elongate entry slots extending parallel to the longitudinal axis of the distal tip to allow for some radial movement of the spline elements during expansion and contraction, but still restrain their movement circumferentially about the longitudinal axis.

Because of the relatively small sizes and tight tolerances required, the distal tip members are constructed using high precision computer-controlled tools. Cylindrical blanks are first machined, and then the individual passages are machined through the blanks to produce the finished desired tips. This manufacturing process requires machining the first passage, including the required recess and/or elongate slots, indexing the cylindrical body both radially and axially, and then repeating the process sequentially for each additional passage. Thus, the Constellation™ distal tips are highly specialized and relatively expensive components to manufacture.

Accordingly, it would be desirable to provide a distal tip for basket assemblies that may be less expensive and/or easier to make.

SUMMARY OF THE INVENTION

The present invention is directed to a flexible distal tip for securing a plurality of spline elements forming a basket assembly for use on an invasive catheter. In a preferred embodiment, the distal tip includes a tip body formed from a substantially flexible material, and defining an axis. The tip body includes a plurality of radially extending passages, which intersect the axis, and which are spaced apart axially from one another along the axis. In particular, the passages are configured to accommodate the plurality of spline elements, such that the spline elements are fixed by the distal tip proximate their respective midpoints.

The distal tip preferably has a substantially cylindrical shape, and is formed from a flexible, resilient vulcanized material, such as silicone. Each of the passages may include a recess configured for receiving a notch formed in the corresponding spline element retained therein.

In accordance with a preferred method of manufacture, a distal tip is formed using a molding process, which includes wrapping a plurality of spline elements around a tool or mandrel, wherein the spline elements intersect within a cavity at an apex of the tool, the apex defining the axis. An uncured material, such as silicone, is introduced into the cavity to encapsulate the spline elements therein. The material is then cured to form the plurality of spline passages around the spline elements themselves. Preferably, the tool includes a plurality of grooves intersecting at the apex, thereby allowing individual spline elements to be placed in respective individual grooves, such that midpoints of the spline elements overlie the axis.

In one preferred embodiment, the distal tip is incorporated into a distal basket assembly of an electrophysiology catheter, including an elongate catheter body defining a longitudinal axis between proximal and distal ends thereof, the distal end being adapted for insertion into a blood vessel. A plurality of loop-shaped spline elements extend from the distal end and together define a generally spherical shape having an apex intersected by the longitudinal axis. Preferably, each spline element has a midpoint between first and second ends thereof, the first and second ends being attached to the elongate catheter body, such that the midpoints intersect along the longitudinal axis. The flexible distal tip is provided at the apex, bonding the spline elements at their midpoints. The spline elements may each carry a plurality of electrodes configured for making contact with internal body tissue.

During use, the spline elements may be directed between contracted and expanded conditions. In accordance with one aspect of the present invention, the distal tip resiliently yields when the spline elements are directed between the contracted and expanded conditions, thereby minimizing stress in the spline elements.

Other objects and features of the present invention will become apparent from consideration of the following description taken in conjunction with the accompanying drawings.

DETAILED DESCRIPTION OF THE PREFERRED EMBODIMENTS

Figure 1:
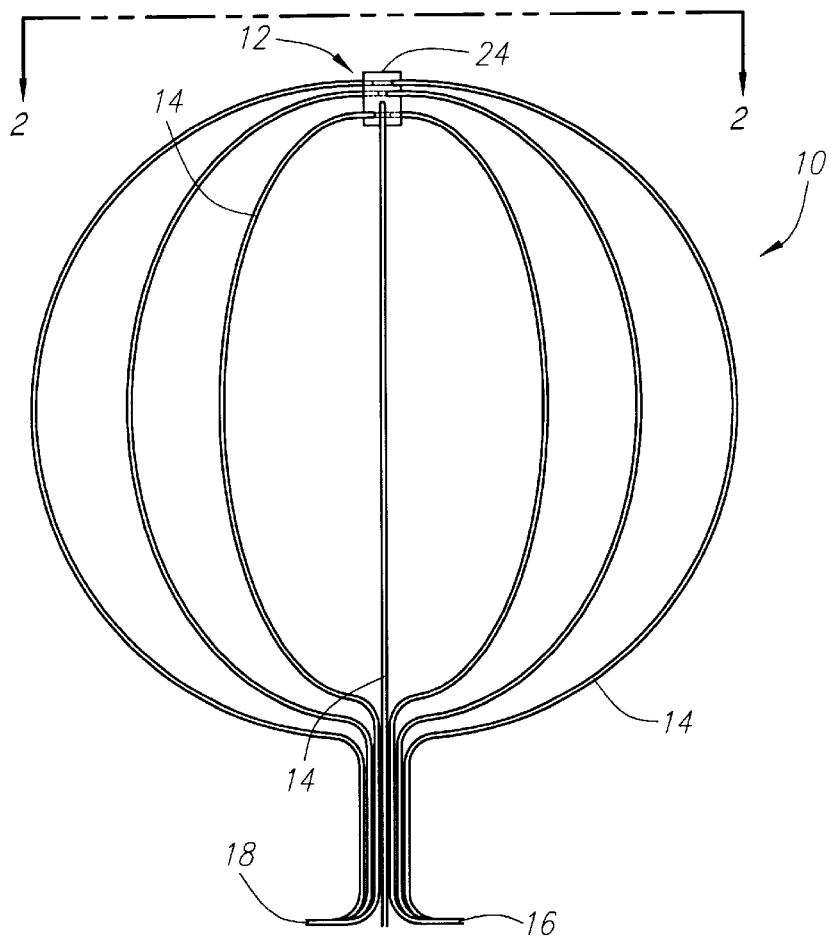
FIG. 1 is a side view of a basket assembly formed by a plurality of flexible spline elements looped from the end of a catheter, with a flexible distal tip securing the spline elements at their respective midpoints.
Figure 2:
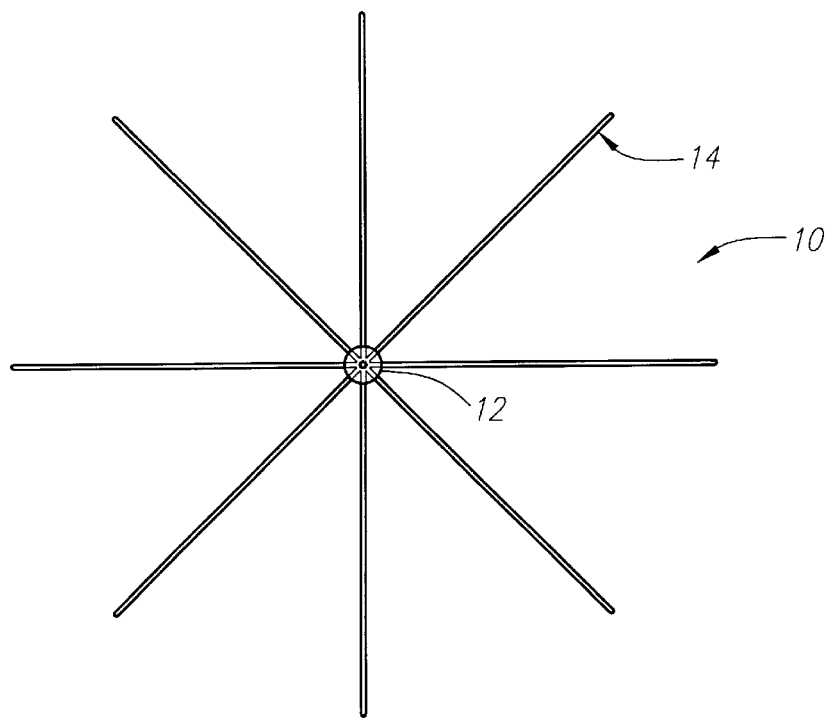
FIG. 2 is a top view of the basket assembly of FIG. 1.
Figure 3:
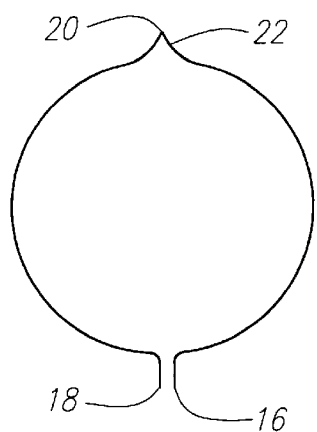
FIG. 3 is a side view of an individual spline element in the basket assembly of FIG. 1.

Turning to the drawings, FIGS. 1–4 show a preferred embodiment of a basket assembly 10 formed by a plurality of flexible spline elements 14, with a flexible distal tip 12 securing the spline elements 14. As best seen in FIG. 3, each spline element 14 has a first end 16, a second end 18, and a midpoint 20 including a notch 22. The first and second ends 16, 18 are adapted to be attached to a catheter body (not shown) such that a longitudinal axis 22 is defined between the ends 16, 18 and the midpoints 20. Preferably, the basket assembly 10 includes four spline elements 14 as shown, although fewer or additional spline elements may be provided. In addition, although a circular shape is shown, it will be appreciated that the spline elements 14 may have a variety of curved, elliptical or other loop shapes, that may together define a three-dimensional and/or generally spherical basket assembly 10.

Figure 4:
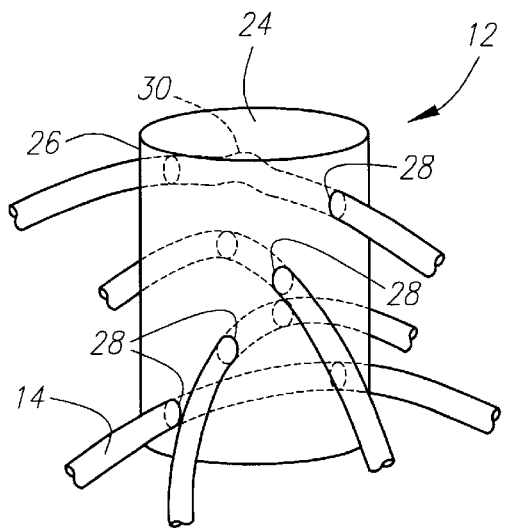
FIG. 4 is a perspective view of the flexible distal tip of FIG. 1, illustrating respective spline passages and spline elements therethrough in phantom.

With particular reference to FIG. 4, the distal tip 12 is a substantially cylindrical body 26 for securing the spline elements 14 about the longitudinal axis 24. The cylindrical body 26 is formed from a substantially flexible, resilient material, and includes a plurality of spline passages 28 extending radially therethrough and intersecting the longitudinal axis 24. The spline passages 28 are preferably spaced apart from one another along the longitudinal axis 24 to substantially isolate the spline elements 14 from one another, and are preferably circumferentially spaced apart evenly about the longitudinal axis 24. Preferably, each spline passage 28 includes a recess 30 therein for receiving the notch 22 on the corresponding spline element 14, for example, to substantially secure the midpoint 22 of the spline element 14 in alignment with the longitudinal axis 24, and thereby prevent the spline elements 14 from sliding out of respective spline passages 28.

The distal tip 12 is preferably formed from a molded and/or vulcanized material, more preferably silicone, that is safe for introduction into the human body. Alternatively, other materials may be used to form the distal tip 12, such as rubber, low durometer (soft) urethane plastic or other elastomeric polymers, which may provide the desired flexibility and resiliency. In addition, although a cylindrical shape is preferred for the distal tip 12, other three-dimensional forms, such as an octagonal or spherical structure, may also be effective for securing the spline elements 14 yet accommodating radial bending of the spline elements 14 during use.

Figure 5:
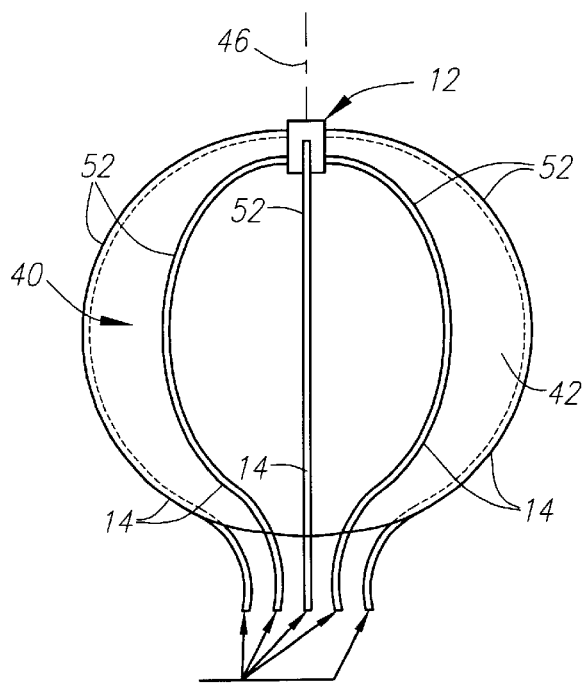
FIG. 5 is a side view of a plurality of spline elements placed in a tool and having a flexible distal tip being molded thereon for manufacturing the assembly of FIG. 1.
Figure 6:
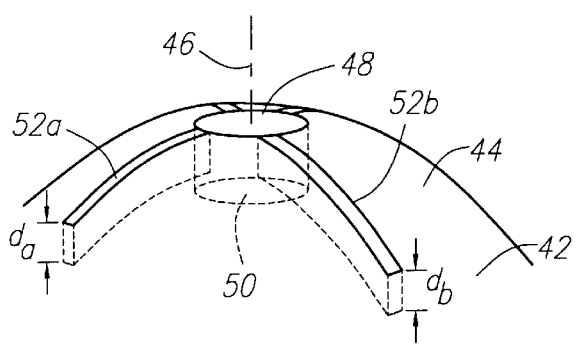
FIG. 6 is a detailed perspective view of the tool of FIG. 5, showing a tip cavity and grooves for receiving respective spline elements.

Turning to FIGS. 5 and 6, a tool or mandrel 40 is shown for use in forming a distal tip 12 in accordance with a preferred method of manufacture. The tool 40 is a substantially spherical body 42 having a convex outer surface 44, and defining an axis 46 substantially normal to an apex 48 thereof. Alternatively, the tool 40 may define only a portion of a sphere, an ellipse or similar curved surface (not shown). The tool 40 is preferably made from a polished steel coated with a mold release to facilitate removal of the finished distal tip 12.

A cavity 50 extends into the tool 40 at the apex 48 substantially along the axis 46, the cavity 50 having a shape corresponding to the desired shape of the distal tip 12, e.g., a substantially cylindrical shape. A plurality of grooves 52 for receiving the spline elements 14 extend along the outer surface 44, intersecting at the apex 48 within the cavity 50. Preferably, the grooves 52 are circumferentially spaced evenly about the axis 46 to correspond substantially to the circumferential spacing of the spline elements 14 about the longitudinal axis 24.

In addition, the grooves 52 preferably have different depths that correspond substantially to the axial spacing of the spline elements 14 along the longitudinal axis 24 (shown in FIG. 4). For example, as seen in FIG. 6, which shows only two grooves 52a, 52b for illustrative purposes, the grooves 52a, 52b have different depths da and db respectively.

With particular reference to FIG. 5, a distal tip 12 may be formed by wrapping the spline elements 14 around the tool 40, preferably by placing and seating individual spline elements 14 fully within each of the grooves 52 such that the spline elements 14 intersect the axis 46 within the cavity 50. Preferably, the midpoints 20 of the spline elements 14 all intersect the longitudinal axis 46 within the cavity 50. More preferably, because of the different depths of the grooves 52, the fully seated spline elements 14 intersect the axis 46 within the cavity 50 at different depths therein, thereby aligning the midpoints 20 of the spline elements 14 axially along the axis 46.

The tool 40 is placed in a mold (not shown), and liquid or uncured silicone is then introduced into the cavity 50. The cavity 50 is substantially completely filled to encapsulate the midpoints 20 of the spline elements 14 within the silicone. The silicone is then cured, to thereby form a distal tip 12 within the cavity 50 that is substantially bonded to the spline elements 14. For example, in a preferred curing method, the mold may be heated to a temperature of between about 350° F. and about 450° F. for between about 15 and about 30 seconds.

As the silicone is cured, the spline passages 28 are also formed directly around the spline elements 14 themselves. Preferably, the spline elements 14 includes notches 22 on their midpoints 20 that create corresponding recesses 30 within the passages 28, thereby substantially securing the spline elements 14 within the distal tip 12. Alternatively, the bonding between the silicone of the distal tip 12 and the spline elements 14 is made sufficiently strong, the recesses 30 and corresponding notches 22 may not be needed.

The spline elements 14 and the cured distal tip 12 may then be removed from the tool 40 and incorporated into a method for making an invasive catheter device. For example, each spline element 14 may be at least partially covered with a thin tube of Pellethane polyurethane or similar plastic material (not shown), and a plurality of electrodes (not shown) may be attached to or otherwise disposed along the spline elements 14. The first and second ends 16, 18 may be attached to an elongate catheter body, and inserted into a guide sheath or delivery catheter, which may constrain the basket assembly 10 for delivery into a patient's body (not shown).

Thus, a distal tip in accordance with the present invention is formed in a simplified process that substantially secures the spline elements of a basket assembly directly within the distal tip. The spline elements are substantially bonded to the distal tip, thereby minimizing misalignment both circumferentially, i.e., about the longitudinal axis, and transversely, i.e., from the spline elements sliding out of the passages in which they are encapsulated.

Because of the flexible and resilient properties of the distal tip, the stress on the spline elements is substantially minimized during use of the basket assembly, i.e., when the spline elements are directed between contracted and expanded conditions. For example, when a basket assembly with a flexible distal tip is inserted into a guide sheath, the spline elements assume a contracted condition, i.e., the spline elements are compressed radially inward. The flexible distal tip of the present invention surrounds and secures the spline elements yet is sufficiently flexible to yield to provide a substantially smooth and continuous radius along the spline elements, rather than risking abrupt bends where the spline elements exit the spline passages in the distal tip. The resiliency of the silicone used to form the distal tip also allows the distal tip to substantially recover when the basket assembly is deployed and the spline elements resiliently adopt their expanded condition, which may also minimize wear between the spline elements and the distal tip.

Finally, a flexible distal tip in accordance with the present invention may also provide an improved substantially atraumatic distal tip. The silicone of the distal tip may engage tissue within the body, e.g., within a lumen of a blood vessel and/or within a heart chamber, with substantially reduced risk of abrading, cutting or otherwise damaging the tissue.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A catheter assembly, comprising:

an elongate catheter body defining a longitudinal axis between proximal and distal ends thereof;

a plurality of loop-shaped spline elements attached to the distal end of the catheter body, the spline elements defining a generally spherical shape, each spline element having a midpoint between first and second ends thereof, the respective first and second ends of the spline elements being attached to the catheter body, with the respective midpoints of the spline elements intersecting along the longitudinal axis and being spaced apart from one another along the longitudinal axis, the spline elements being directable between contracted and expanded conditions; and a substantially flexible distal tip member molded to the respective midpoints of the spline elements, each of the spline elements being substantially isolated from one another within the tip member, the tip member resiliently yielding when the spline elements are directed between the contracted and expanded conditions.

2. The catheter assembly of claim 1, wherein the distal tip member comprises a vulcanized material.

3. The catheter assembly of claim 1, wherein the distal tip member comprises silicone.

4. The catheter assembly of claim 1, wherein the spline elements carry a plurality of electrodes.

5. The catheter assembly of claim 1, wherein the distal tip member includes a plurality of independent passages therethrough for receiving respective spline elements, the passages resiliently yielding when the spline elements are directed between the contracted and expanded conditions.

* * * * *